US008923994B2

(12) United States Patent
Laikari et al.

(10) Patent No.: US 8,923,994 B2
(45) Date of Patent: Dec. 30, 2014

(54) PHYSICAL ACTIVITY-BASED DEVICE CONTROL

(75) Inventors: Arto Laikari, VTT (FI); Miikka Ermes, VTT (FI); Lauri Repokari, VTT (FI); Teemu Haapala, VTT (FI); Juhani Harvela, VTT (FI)

(73) Assignee: Teknologian Tutkimuskeskus VTT, VTT (FI)

( * ) Notice: Subject to any disclaimer, the term of this patent is extended or adjusted under 35 U.S.C. 154(b) by 0 days.

(21) Appl. No.: 13/511,149

(22) PCT Filed: Nov. 23, 2010

(86) PCT No.: PCT/FI2010/050954
§ 371 (c)(1),
(2), (4) Date: May 22, 2012

(87) PCT Pub. No.: WO2011/061412
PCT Pub. Date: May 26, 2011

(65) Prior Publication Data
US 2012/0239173 A1 Sep. 20, 2012

(30) Foreign Application Priority Data
Nov. 23, 2009 (FI) ..................................... 20096232

(51) Int. Cl.
*G06F 19/00* (2011.01)
*A61B 5/11* (2006.01)
*A61B 5/00* (2006.01)
*A63B 24/00* (2006.01)

(52) U.S. Cl.
CPC .............. *A61B 5/1118* (2013.01); *A61B 5/1112* (2013.01); *A61B 5/1123* (2013.01);
(Continued)

(58) Field of Classification Search
CPC ... A61B 5/1118; A61B 5/7239; A61B 5/7267
See application file for complete search history.

(56) References Cited

U.S. PATENT DOCUMENTS

2002/0107649 A1 8/2002 Takiguchi et al.
2005/0172311 A1* 8/2005 Hjelt et al. ...................... 725/10
(Continued)

FOREIGN PATENT DOCUMENTS

GB         2447647        9/2008
WO         2007/062102    5/2007

OTHER PUBLICATIONS

Jennifer R. Kwapisz, Gary M. Weiss, and Samuel A. Moore "Cell Phone-Based Biometric identification" J. R. Kwapis2, G. M. Weiss, and S. A. Moore are with the Department of Computer & Information Science, Fordham University, Bronx, NY 10458, USA {kwapis2, gweiss, asamoore}@cis.fordham.edu, 978-I-4244-758G-3/10/$26.00 © 2010 IEEE.

(Continued)

*Primary Examiner* — David L Lewis
*Assistant Examiner* — Shauna-Kay Hall
(74) *Attorney, Agent, or Firm* — Mark M. Friedman

(57) ABSTRACT

A method for controlling the configuration, such as access and/or one or more other features, of an application in an electronic device from the standpoint of a particular user, comprising obtaining an indication of the identity of the user determined based on sensor data associated with physical activity by the user, obtaining an indication of the physical activity identified based on the sensor data, and modifying or at least providing information enabling to modify the identified user's configuration of an application logic based on the identified activity and optionally other activity information derived utilizing the sensor data. Related mobile device, electronic arrangement and system are presented.

21 Claims, 7 Drawing Sheets

(52) U.S. Cl.
CPC ........... *A61B 5/6898* (2013.01); *A63B 24/0062* (2013.01); *A61B 2562/0219* (2013.01); *A61B 2562/0247* (2013.01); *A63B 2024/0065* (2013.01); *A63B 2024/0068* (2013.01); *A63B 2220/30* (2013.01); *A63B 2220/40* (2013.01); *A63B 2220/803* (2013.01); *A63B 2220/833* (2013.01); *A63B 2225/50* (2013.01); *A63B 2230/04* (2013.01); *A63B 2230/30* (2013.01); *A61B 5/7239* (2013.01); *A61B 5/7267* (2013.01)
USPC ............................................... 700/91; 482/2

(56) References Cited

U.S. PATENT DOCUMENTS

| | | | | |
|---|---|---|---|---|
| 2006/0080551 | A1* | 4/2006 | Mantyjarvi et al. | 713/186 |
| 2007/0208544 | A1* | 9/2007 | Kulach et al. | 702/189 |
| 2007/0276295 | A1* | 11/2007 | Shugg | 600/595 |
| 2008/0077489 | A1* | 3/2008 | Gilley et al. | 705/14 |
| 2008/0096726 | A1* | 4/2008 | Riley et al. | 482/8 |
| 2008/0175443 | A1* | 7/2008 | Kahn et al. | 382/115 |
| 2008/0176655 | A1* | 7/2008 | James et al. | 463/42 |
| 2008/0182727 | A1* | 7/2008 | Uang | 482/54 |
| 2010/0105525 | A1* | 4/2010 | Thukral et al. | 482/8 |
| 2010/0125028 | A1* | 5/2010 | Heppert | 482/8 |
| 2011/0018682 | A1* | 1/2011 | Weisfeld | 340/5.7 |
| 2011/0152637 | A1* | 6/2011 | Kateraas et al. | 600/301 |
| 2011/0191158 | A1* | 8/2011 | Kateraas et al. | 705/14.27 |

OTHER PUBLICATIONS

Nicholas D. Lane, Emiliano Miluzzo, Hong Lu, Daniel Peebles, Tanzeem Choudhury, and Andrew T. Campbell, Dartmouth College "A Survey of Mobile Phone Sensing" AD Hoc and Sensor Networks, IEEE Communications Magazine• Sep. 2010, pp. 140-150.

Myong-Woo Lee, Student Member, IEEE, Adil Mehmood Khan, Ji-Hwan Kim, Student Member, IEEE, Young-Sun Cha, and Tae-Seong Kim, Alel1Iber, IEEE :"A Single Tri-axial Accelerometer-based Real-time Personal Life Log System Capable of Activity Classification and Exercise Information Generation", 32nd AnnualInternational Conference of the IEEE EMBS Buenos Aires, Argentina, Aug. 31-Sep. 4, 2010, pp. 1390-1393.

Jani Man1}jarvi, Mikko Lindholm, Elena Vildjiounaite, Satu-Marja Makela, Heikki Ailisto :"Identifying Users of Portable Devices From Gait Pattern With Accelerometers" ,VTT Electronics Qulu, Finland, © 2005 IEEE, pp. 973-976.

Hari Thiruvengada, Soundararajan Srinivasan and Aca Gacic :"Design and Implementation of an Automated Hun1an Activity Monitoring Application for Wearable Devices" 2008 IEEE International Conference on Systems, Man and Cybernetics (SMC 2008), pp. 2252-2258.

Yun, J.et al. User Identification Using User's Walking Pattern over the ubiFloorII. In : Computational Intelligence and Security, Springer Berlin/Heidelberg, Jun. 18, 2006. vol. 3801/2005, pp. 949-956.

* cited by examiner

PHYSICAL ACTIVITY-BASED DEVICE CONTROL

FIELD OF THE INVENTION

Generally the invention pertains to monitoring physical activity of a person by one or more sensors. In particular, the invention concerns the control of an electronic device in accordance with the characteristics of the sensor data associated with the physical activity.

BACKGROUND

Notwithstanding the current popularity of health, beauty care and fitness activities, global concern has been growing over the degrading general condition and obesity of population, especially children, which is at least partially due to the various modern transportation aids such as motor vehicles, telecommunication and computer systems such as the e-mail and cellular/landline networks, and the leap in the amount and versatility of available electronic, "virtual, world" entertainment including video games and movies. All these factors, besides their obviously positive effects including time and cost savings or rewarding mental experiences, also unfortunately obviate the need to perform physical tasks as traditionally required for achieving similar goals such as transportation from a place to another, or playing a game with friends. Accordingly, this trend negatively affects the general condition of people. In addition, it is well known fact that excessive video gaming and use of computers in general at the cost of physical exercise and real-life contacts may cause serious social and mental problems to children and adults both alike.

Intimidation of people to work out seldom works for long, however, even if the medical basis and benefits behind the regular physical activity is understood by, at least, most adults and some kids. The reason is that the other pastime options are just too tempting for many of us.

In connection with children and despite the fact their parents may control and, when necessary, limit e.g. television/computer usage by managing hardware and/or software-based child lock functionalities of the relevant gear or by active supervision and upbringing of the kids, for example, such control means and upbringing methodology require a lot of work from the parents and may negatively affect their relationship with the kids.

SUMMARY OF THE INVENTION

The objective is to at least alleviate the problem described hereinabove and to provide a solution that motivates people, such as children, to perform physical exercise.

The objective is achieved by embodiments of a mobile device, an electronic arrangement, a system, and a method in accordance with the present invention. An aspect of the devised solution thus incorporates utilization of a mobile, optionally personal, device comprising or being at least functionally connected to at least one sensor for obtaining data indicative of physical activity associated with the user of the device. The sensor data may be analyzed by the mobile device and/or a number of external devices provided with the data, and various activity information such as related user identity, activity type, and/or energy consumption information may be derived therefrom for controlling the configuration, such as access and/or one or more other features, of the mobile device and/or a number of devices external thereto.

For instance, the identified user's configuration of local and/or external application logic, such as of a computer application, may be adapted based on the activity information such as activity type and/or estimated energy consumption caused by the performed activity. The mobile device and/or the application logic may have a plurality of users. The mobile device may include a mobile terminal, a PDA (personal digital assistant), a wrist computer (wristop), a palmtop, a portable multimedia/music player, a calculator, a digital camera, a dictaphone, or a multi-purpose or dedicated pod apparatus, among other options.

Accordingly, in one aspect of the present invention a mobile device comprises
  a sensor data storage for obtaining sensor data indicative of physical activity associated with a user monitored via a sensor,
  a user recognizer for identifying the user on the basis of the sensor data obtained,
  an activity recognizer for identifying the physical activity on the basis of the sensor data obtained, and
  an interface for providing an indication of the user identity and indication of the identified activity, optionally also other activity information based on the sensor data and/or the sensor data itself, to an application logic to enable modifying the identified user's configuration, such as access and/or one or more other features, relative to the application logic, said application logic being either local or external relative to the mobile device.

In one embodiment the mobile device may contain the sensor. For example, an accelerometer and/or other sensor may be disposed within and/or attached to the housing of the device or any of its elements. Alternatively, the sensor may be an external to the mobile device and functionally connected thereto via a wired or wireless connection. The mobile device may comprise and/or be at least functionally connected to a plurality of sensors. The mobile device may thus support direct context awareness, i.e. it may be self-contained what comes to the sensing entities. Alternatively or additionally, the mobile device may support indirect context awareness, i.e. it receives sensor data from external, functionally connected entities such as external sensor devices at least functionally coupled to the mobile device. At least some of the plurality of sensors may be substantially identical but the configuration thereof, such as settings, orientation and/or placement, may mutually differ. Some of the sensors may be mutually substantially different and be configured to measure different quantities.

For example, the sensor(s) may include at least one element selected from the group consisting of: an accelerometer, a gyroscope, a pedometer, a pulse meter (heart rate meter), a movement sensor, a pressure sensor, a location sensor, a distance sensor, velocity sensor, a speed sensor, and a blood oxygen sensor. Also, an imaging sensor such as a camera sensor (e.g. CMOS) may be applied. A sensor and optionally the mobile device comprising the sensor may be located, such as attached, directly to a user or his/her clothing including shirts, jackets, pants, headpiece such as a cap or a headband, footwear etc. such that the user ultimately carries the sensor, or the user may otherwise interact with the sensor. As one example, e.g. a pressure sensor may be located under the user, potentially within/under a carpet or mattress such that the related sensor data is created upon physical activity. As another example, an acceleration sensor may be configured to measure the acceleration of trunk, chest, waist, head, limb, and/or other target part of the user during the monitored physical activity.

In one alternative or supplementary embodiment the sensor data originating from one or more sensors may be stored in the storage, preferably in a digital form. The sensor data may be obtained an/or stored in a form of samples representing a value of a measured quantity relative to time, frequency and/or some other reference. The sensor data may be pre-processed upon capture or at some other feasible instant. For instance, filtering of the sensor signal(s) and/or extracting a number of representative parameters therefrom may be included in the pre-processing. Sensor data entities, such as samples and parameters, may temporally represent a monitoring period of a fixed or dynamic length. Monitoring of the fulfillment of trigger condition(s) may be used to trigger the acquisition and/or terminate the acquisition of sensor data. After fulfillment of a triggering condition with no terminate condition, the sensor data may be gathered for a predetermined, fixed or dynamic, duration. At other times the sensor may remain in a sleep state. Alternatively or additionally, substantially continuous monitoring of the user via the sensor(s) may be applied. Optionally a sensor applies adaptive measurement frequency and/or accuracy, which may depend on the nature or amount of detected activity events, for example.

Further, in one alternative or supplementary embodiment the user recognizer may be configured to identify the user associated with particular sensor data, i.e. the person whose physical activity has been monitored by the sensor(s). The applied resolution may be user-specific and/or user class or user group-specific or defined otherwise. The user recognizer may apply some already available solution for the task, or a proprietary solution may be designed. As one option, the user recognizer may exploit sensor data created by movement sensor(s), e.g. the aforementioned acceleration sensor(s) and optionally a number of other sensors.

Each user may be associated with at least one stored reference, e.g. a reference signal, whereto the sensor data and/or information derived therefrom, such as one or more parameters, are compared. The user recognizer may be taught, or "trained", by indicating thereto a certain user and providing the activity sensor data associated with the user so as to enable the recognizer to establish the user-specific reference (signal). For instance, one reference (signal) per activity (type) to be identified per user may be utilized. Reference and current comparison data including and/or being based on the sensor data may be formed similarly. They may correspond to a time period of similar length, for example. The user recognizer may apply at least one analysis method or tool for performing comparison tasks selected from the group consisting of: cross correlation, Fourier coefficients, neural network, and structured pattern recognition. The stored reference (signal) may be offset for comparison in a predetermined manner, e.g. in discrete steps, so as to improve the recognition process. Offset may be temporal offset relative e.g. to the order or selection of time-domain sample or related parameters, or a value-related offset, e.g. increase/decrease in sample or parameter values, for instance. The user with a reference (signal) matching best with the current comparison data may be determined as the recognized identity. User-reference (signal) associations may be maintained by the user recognizer e.g. in a table, database and/or other data entity. The user recognizer may utilize at least one user-specific reference (signal) for each of a plurality of users.

In one alternative or supplementary embodiment the activity recognizer, as a logical entity like the user recognizer, may perform independent from or collaboratively with the user recognizer. In case the reference signal is provided per each user and each activity type, user recognition and activity recognition may be jointly executed and may comprise one or more common procedure(s). The activity-specific reference signal forming a best match with the current comparison data may then indicate the recognized activity type in addition to the user identity, advantageously from a plurality of user and/or activity options. Activity-reference (signal) associations may be maintained by the activity recognizer e.g. in a table or some other data entity. A joint data entity such as a table may host both user-reference and activity-reference associations. Alternatively, the activity recognizer may be executed substantially independently from the user recognizer.

The sensor data signal may be segmented into a number of activity periods (with determined beginning/end points) using a predetermined segmentation method. Subsequently the activity periods and the underlying physical activity may be classified using a selected, already known or a proprietary, activity recognition algorithm. For example, the activity recognizer may comprise at least one element selected from the group consisting of: a neural network, a linear classifier, and a Bayesian classifier. The recognizer may be trained by providing training data from a plurality of physical activities together with correct indications of the activity to the recognizer that adapts to the training data. Activity types to be identified may include, but are not limited to, walking, running, cycling, sitting, rowing, jumping, crawling, playing football, playing ice hockey and/or one or more other physical, e.g. sports, activities. Alternative partitioning of activities may be utilized; for example, division into low-level activities such as sitting or standing, medium-level activities such as many household activities or walking, and high-level activities such as many sports, may be applicable. Such division and relating activity resolution obtained may be depend on the estimated average energy consumption of the activities, for instance.

More specific activity types may be grouped together to form new (aggregate) activity types. Also essentially inactivity and optionally sub-types thereof (laying, standing, etc.) may be detected from the sensor data and considered as at least one activity (type). In a basic scenario, at least the periods of physical activity and inactivity/passivity may be identified from the sensor data. The activity recognizer may then utilize at least one activity-specific reference (signal) for each of a plurality of activities, optionally user-specifically. The reference may include a centroid of an activity type class of a centroid-based classifier included in the recognizer, for example.

In one alternative or supplementary embodiment the other activity information may include further qualitative and/or quantitative information indicative of the nature of the activity such as frequency, duration, intensity, energy consumption and (physical) stressfulness thereof. The indication may include numeric, symbolic and/or textual indication e.g. on a predetermined scale and/or following a predetermined syntax, for example. Determination of the activity information may be optionally at least partially built on cycle-based and/or other analysis of the sensor data, e.g. analysis of the aforesaid segments. Such information may be optionally at least partially based on predetermined data linked to the identified user and/or physical activity type. The mobile device may comprise an analyzer entity for providing the qualitative and/or quantitative information used for application logic (and thus related device) control. Physical activity recommendations may be produced to the user(s) based on analyzed sensor data and optionally other factors.

In one alternative or supplementary embodiment the interface comprises an interface internal to the mobile device, i.e. the application also resides therein. Alternatively or additionally, the interface may connect the device to external devices such as one or more computers, game consoles, and/or aggregate entities such as network(s). The interface may be a logical interface transferring sensor data and/or activity information towards one or more applications for control, analysis, data logging, and/or other purposes. The interface may comprise logic, e.g. software logic, and optionally hardware elements such as terminals, electronic components, chips and conductors/pins. It may comprise a wireless and/or wired transceiver, for example. The interface may include at least one element selected from the group consisting of: a WLAN (Wireless LAN) transceiver, a LAN (Local Area Network) interface (e.g. Ethernet), a USB (Universal Serial Bus) interface, a serial interface, a cellular transceiver such as GSM (Global System for Mobile Communications) or UMTS (Universal Mobile Telecommunications System) transceiver, a memory card interface, a memory stick interface, a hard disk interface, an optical media (e.g. CD-ROM) interface, a floppy interface, a Bluetooth transceiver, an infrared transceiver or transmitter, and an ultrasound transceiver or transmitter.

In one alternative or supplementary embodiment the mobile device may comprise at least one remote identification tag such as an NFC (Near Field Communication) tag and/or RFID (Radio Frequency Identification) tag preferably provided with advantageously unique ID. The mobile device may also comprise a corresponding reader. The ID may be transferred to an external device, optionally in response to a query and/or power-up by the external device. The interface may comprise the tag and utilize it for the sensor data, activity information and/or related control information provision towards external device(s).

In one alternative or supplementary embodiment the application logic utilizing the received sensor data, user identity, activity type, and/or other activity information may implement at least one application class selected from the group consisting of: a parental control application, an access control application, a feature control application, a data logging application, a fitness/sports application, and a game application. Access and/or one or more features may be controlled by the activity information, for instance. The application logic may be configured to control one or more other applications (logics).

The application (logic) may include at least one element selected from the group consisting of: a parental control feature, a game feature, a personal training feature, a training log, a locked feature, a reward feature, a punishment feature, a bonus feature, activation feature, deactivation feature, an instructive feature, a communication feature, and an encouraging feature. The sensor data or related activity information (user identity, activity type, and/or other activity information as reviewed above) may be used for defining the future state of the element. For example, activity information indicative of e.g. predetermined activity type, user, and/or energy consumption fulfilling one or more requirements, such as exceeding or remaining below a threshold, may trigger enabling, disabling, or changing the user's access to the application or enabling, disabling, or changing a functionality/feature thereof, such as access relative to content of the application and/or to a second application at least partially controlled by the application. For example, the (first) application may implement a parental control application regulating access to the second application and optionally one or more further applications. Correspondingly, as an application may control the host device thereof, the user's access to the device may be completely or partially, e.g. in view of one or more electronically (computer) controlled hardware and/or software features such as applications, enabled and/or disabled.

In one alternative or supplementary embodiment the activity information or at least part thereof may be stored and/or provided via the interface(s) in XML (Extensible Markup Language) or XML-based format. Alternatively or additionally, at least part of the information and/or sensor data may be stored and/or transmitted as encrypted. Generally the activity information may be gathered in one or more data entities such as activity logs.

In one alternative or supplementary embodiment the activity information such as various qualitative and/or quantitative activity information, identified user identity, and/or activity type, may be utilized for controlling, via the application, the configuration, e.g. one or more functionalities or features of the mobile device and/or a number of devices external thereto. The number of external devices may include at least one device element selected from the group consisting of: a terminal device, a mobile terminal, a consumer electronics device, a PDA, a laptop computer, a desktop computer, a household appliance, a television, a video recorder, CD (Compact Disc) player, CD recorder, a DVD (Digital Versatile Disk) player, a DVD recorder, a DVB (Digital Video Broadcasting) receiver, entertainment electronics device, and a game console (example of entertainment electronics). For example, the household device may include a fridge, a vacuum cleaner, an oven, a microwave oven, a stove, a coffee machine, a water heater/boiler, a security device/system such as a burglar alarm device/system, an air conditioning/ventilation device, a lighting device, or a humidifier. A plurality of mutually similar or different devices optionally at least functionally connected together via communication connection(s) directly or via wireless and/or wired networks, for example, may be included in the number of external devices.

In one alternative or supplementary embodiment the mobile device comprises a location determination entity such as a satellite receiver, preferably a GPS (Global Positioning System) satellite receiver. Alternatively or additionally, a wireless (local area) network, Bluetooth, and/or a cellular network based positioning functionality may be applied for locating the mobile device. Location information may be obtained periodically or upon a detected occurrence of a predetermined trigger, such as a detection of general or specific physical activity or inactivity start/end, for instance. Location information may be analyzed and one or more parameters such as velocity, speed, acceleration, travelled distance, and/or travelled course may be derived. Location-based information may be included in the activity information. At least part of the other activity information may be tagged with the location information and/or derived one or more parameters. Location information and/or derived one or more parameters may be transferred via the aforementioned or some other interface to the application.

In one alternative or supplementary embodiment, a plurality of mobile devices may be conceptually mated together. An entity such as an electronic device may collect activity information and/or sensor data from a plurality of personal mobile devices and establish, by the existing user group definitions, for example, user group-specific activity information such as joined activity figures to enable up-lifting the motivation for group training and even subsequent group-based or group activity-based exploitation of target application(s).

In another aspect of the present invention, an electronic arrangement, such as an electronic device or a plurality of devices, for controlling and optionally hosting one or more applications comprises an input collector for obtaining sensor data acquired by a mobile device and indicative of physical activity associated with a user, such as sports activity, a user recognizer for identifying the user of the mobile device on the basis of the sensor data, an activity recognizer for identifying the physical activity on the basis of the sensor data, and a control entity configured to modify or at least provide information enabling to modify the identified user's configuration of an application logic based on the identity of the activity and optionally other activity information derived utilizing the sensor data, said application logic being either local or external relative to the electronic arrangement.

The electronic arrangement, such as a computer or other electronic device, may co-operate with an embodiment of the afore-explained mobile device or some other mobile device comprising at least one sensor or being at least functionally connected to one or more sensors. The electronic arrangement may include a terminal device, a network device, or a plurality of at least functionally, possibly indirectly interconnected (e.g. via network(s)) devices such as cloud computing devices. The electronic arrangement may include a game console or other entertainment electronics device. The electronic arrangement may include a server device. The electronic arrangement may contain a computer game or other application to be controlled by the physical activity. The electronic arrangement may include a household device. The electronic arrangement may incorporate a parental control application logic comprising the control entity and optionally further comprising or at least utilizing the activity recognizer, the user recognizer, and/or the input collector.

In some embodiments, the electronic arrangement may further comprise an analyzer for determining desired quantitative and/or qualitative activity information based on the sensor data. As described with reference to the mobile device, the activity information may include information indicative of the nature of the activity such as frequency, duration, intensity, energy consumption and (physical) stress fulness thereof. The indication may include numeric, symbolic and/or textual indication e.g. on a predetermined scale/following a predetermined syntax, for example.

For instance, activity points or credits may be allocated for user's exploitation relative to a target application such as a game. Such information may be optionally at least partially based on cycle-based and/or other analysis of the sensor data, e.g. analysis of the aforesaid segments. Such information May be optionally at least partially based on predetermined data linked to the identified user and/or physical activity type.

In one alternative or supplementary embodiment, the electronic arrangement further comprises an interface for transferring activity information and/or control data derived therefrom to one or more external devices and one or more application logics therein to enable related user-configuration updates.

In a further aspect of the present invention, a system comprises a mobile device and at least one electronic device external thereto, said system further comprising a sensor for obtaining data indicative of physical activity associated with a user, a user recognizer for identifying the user on the basis of the sensor data obtained, an activity recognizer for identifying the physical activity on the basis of the sensor data obtained, and a control entity configured to modify or at least provide information enabling to modify the identified user's configuration of an application logic based on the identity of the activity and optionally other activity information derived utilizing the sensor data.

In one embodiment the mobile device comprises or is at least functionally connected to one or more sensors. In alternative or supplementary embodiment, the mobile device comprises the user recognizer and/or activity recognizer. In alternative or supplementary embodiment, the at least one electronic device includes one or more electronic devices comprising user recognizer, activity recognizer, or both. Such one or more electronic devices may form or belong to a cloud computing entity comprising a plurality of devices. In an alternative or supplementary embodiment, the at least one electronic device includes an application device hosting the application logic but excluding the user recognizer and the activity recognizer; the application device may contain the control entity for modifying the user's configuration based on the activity information or be configured to obtain the related control data from other electronic device comprising the control entity. The at least one electronic device may include an embodiment of the aforesaid electronic arrangement.

Still in a further aspect, a method for controlling the configuration, such as access and/or one or more other features, of an application in an electronic device from the standpoint of a user, comprises obtaining an indication of the identity of the user determined based on sensor data associated with physical activity by the user, obtaining an indication of the physical activity identified based on the sensor data, and modifying or at least providing information enabling to modify the identified user's configuration of an application logic based on the identified activity and optionally other activity information derived utilizing the sensor data.

In one embodiment, the method further comprises obtaining sensor data, such as accelerometer data, indicative of physical activity associated with the user.

In a supplementary embodiment, said obtaining the indication of the user's identity comprises identifying the user on the basis of the sensor data. In alternative or supplementary embodiment said obtaining the indication of the identified physical activity comprises identifying the physical activity on the basis of the sensor data.

In some embodiments all the method steps may be executed by a single device. In other embodiments, a step's execution may be shared and/or the (whole) steps may be divided between a plurality of devices, such as the aforesaid mobile device and the at least one electronic device.

The previously presented considerations concerning the various embodiments of user recognition, activity recognition, other analysis and further features disclosed, such as sensing features and interfacing features, with reference to the mobile device may be flexibly applied to the embodiments of the electronic arrangement, the system, and the method mutatis mutandis and vice versa, as being appreciated by a skilled person.

The utility of the present invention follows from a plurality of issues depending on the particular embodiment. The suggested solution combines physical exercise and electronic entertainment, or generally just the use of electronic appliance(s), in a motivating manner; physical activity may be converted into a desired change in the target application. The present invention thus enables designing applications configured to acquiring indication(s) of user's physical activity as input. The solution may facilitate parental control over the children's computer usage and simultaneously exhort the kids to maintain and even upgrade their condition by rewarding (or punishing) them via feature control in the target electronic appliance. Accordingly, various social and mental problems arising from the excessive video gaming, movie watching, etc. may be cleverly minimized. Different embodiments of the present invention offer highly automated, flexible, and versatile physical activity-based control of electronic devices via the included applications capable of input the related activity and/or control data. Likewise the adults may benefit from the present invention in monitoring the quality and/or amount of performed physical activities. Indeed, different military, security, health (care) and group activities applying more or less tailored embodiments of the present invention may be easily contemplated by a skilled person on the basis of this disclosure.

The expression "a number of" refers herein to any positive integer starting from one (1), e.g. to one, two, or three.

The expression "a plurality of" refers herein to any positive integer starting from two (2), e.g. to two, three, or four.

The expression "application logic" refers herein to any computer software including end-user applications, middleware, system software, and utilities, for example. In addition, the expression may refer to application logic entities such as (re-) programmable logic chips and ASIC (Application-Specific Integrated Circuit) circuits.

Different embodiments of the present invention are disclosed in the dependent claims.

BRIEF DESCRIPTION OF THE RELATED DRAWINGS

Next the invention is described in more detail with reference to the appended drawings in which FIG. 1 illustrates the concept of an embodiment of the present invention.

Figure 4A:
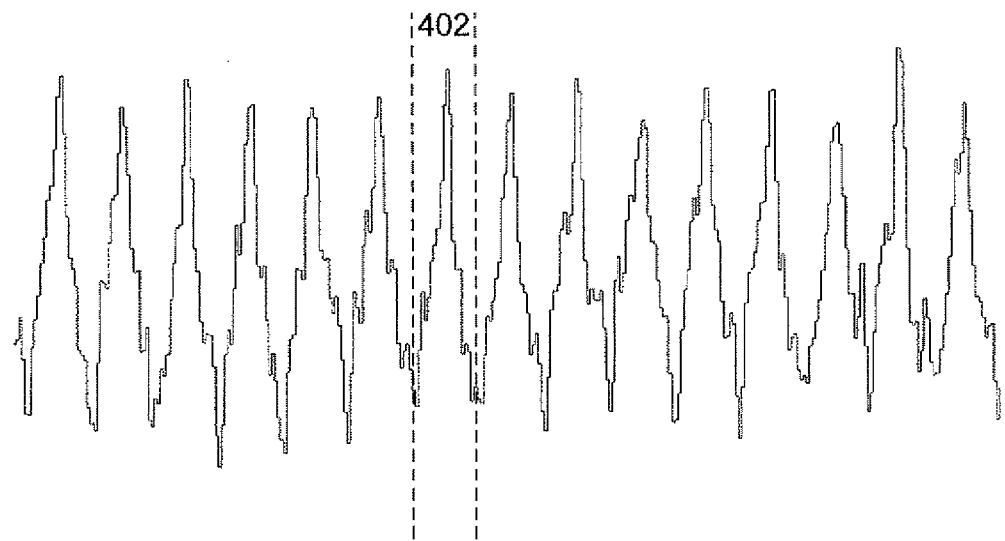
FIG. 4a depicts an example of an accelerometer signal associated with a first physical activity.
Figure 4B:
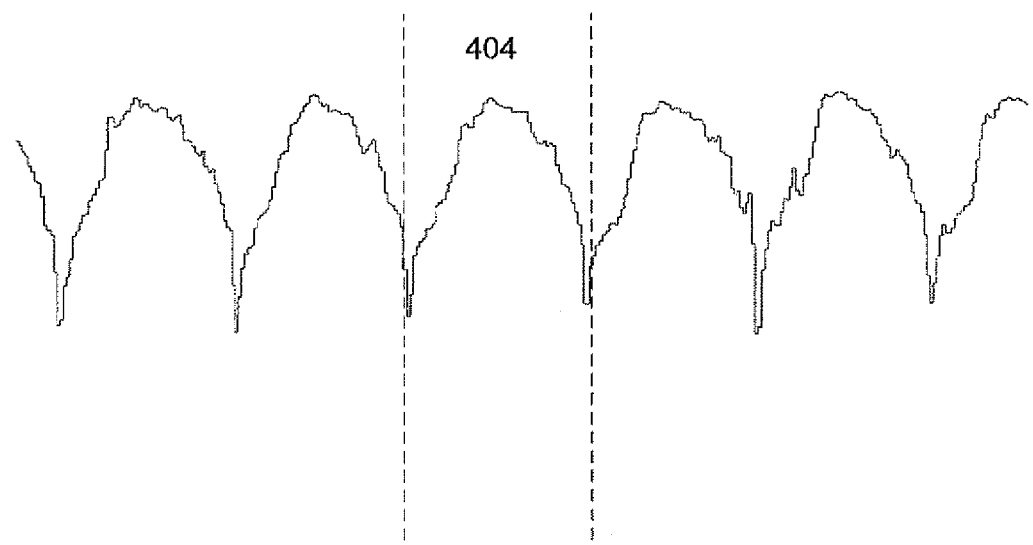
FIG. 4b depicts an example of an accelerometer signal associated with a second physical activity.
Figure 4C:
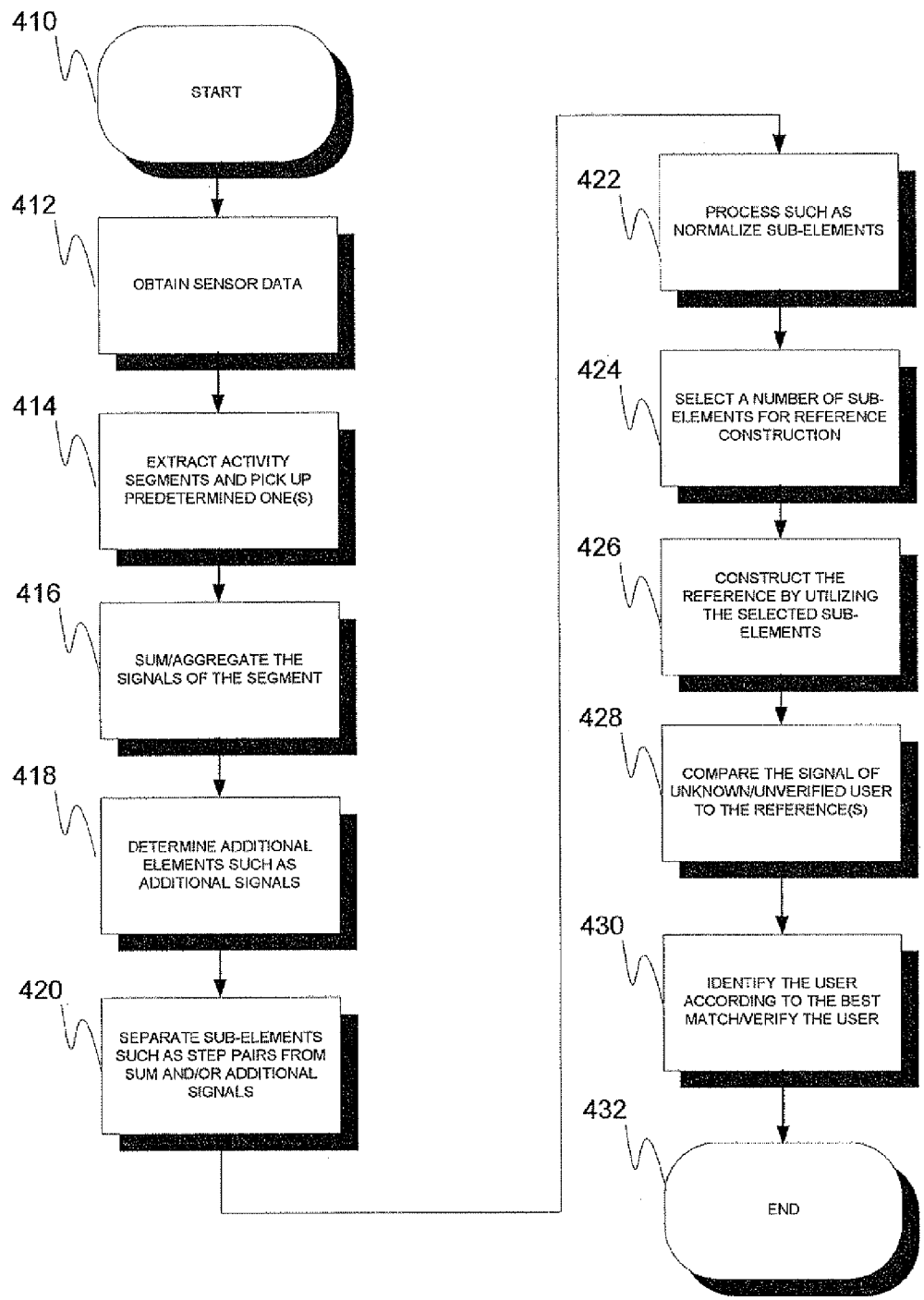
FIG. 4c illustrates an embodiment of a reference signal, or a "reference code", generation method for use in connection with user recognition.
Figure 4D:
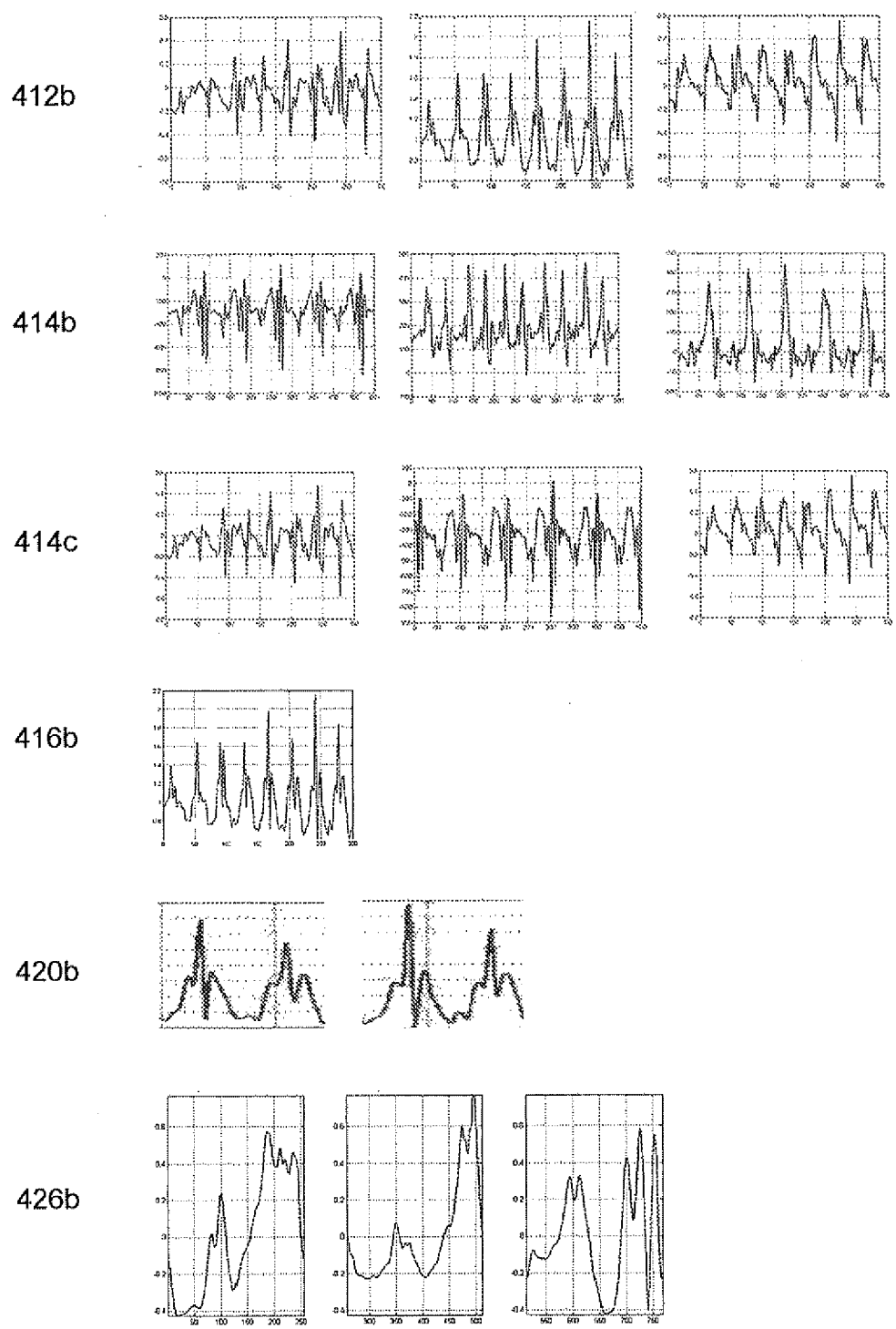

FIG. 4d further illustrates the embodiment of FIG. 4c through visualization of possible, however merely exemplary, signals associated with different method steps.

Figure 5:
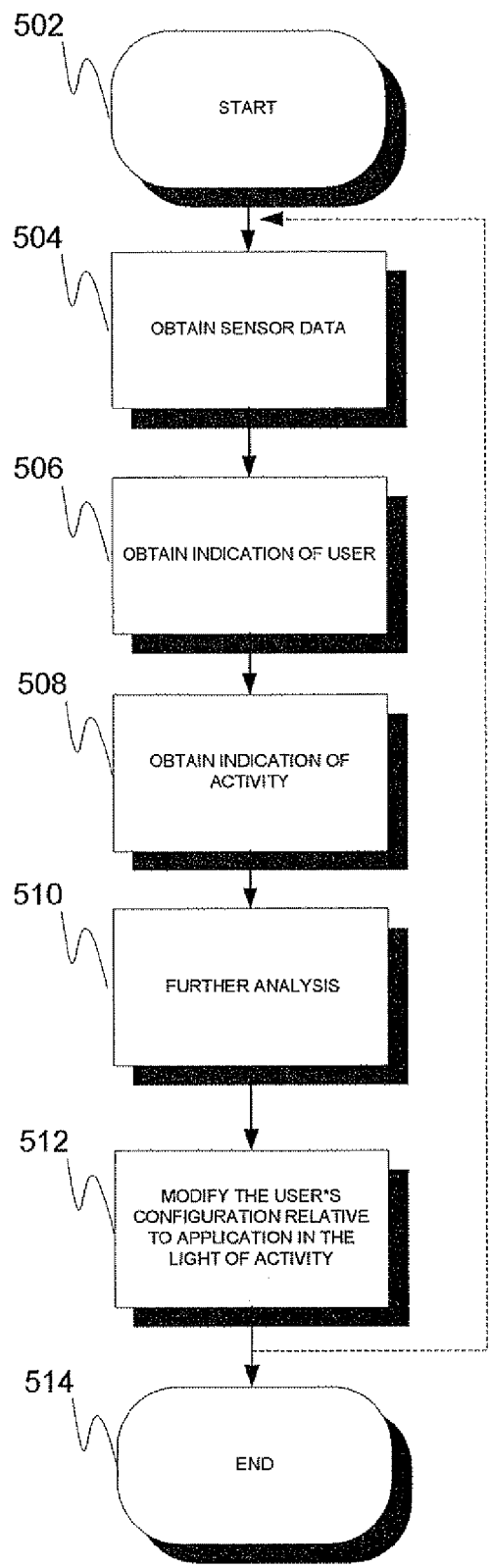

FIG. 5 is a flow chart disclosing an embodiment of a method in accordance with the present invention.

DETAILED DESCRIPTION OF THE EMBODIMENTS

Figure 1:
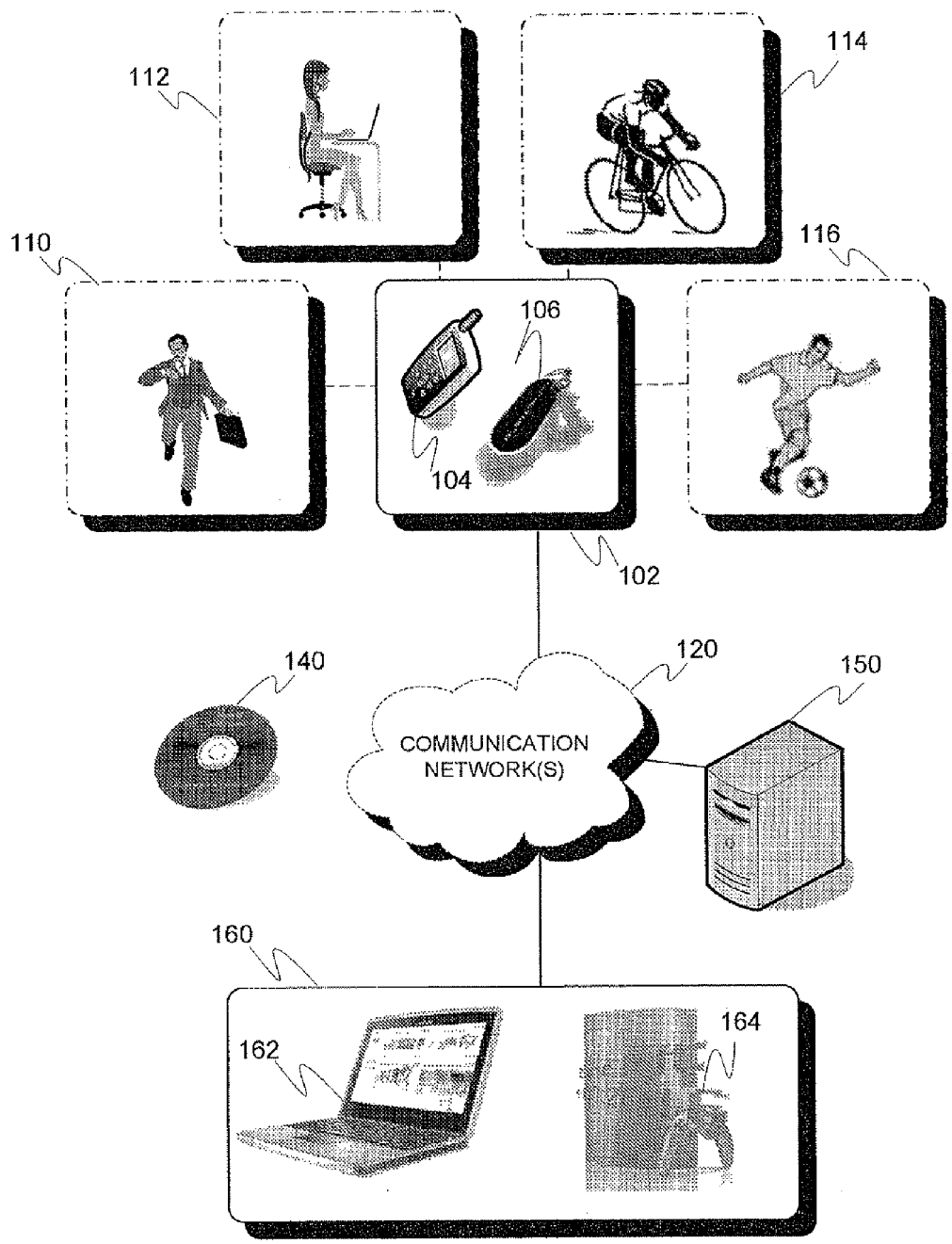

FIG. 1 illustrates the overall concept of the present invention according to an embodiment thereof. A mobile device 102, such as a mobile phone (e.g. a smart-phone) or a PDA (personal digital assistant) 104, or a pod 106, is provided with or at least connected to one or more physical activity sensors monitoring the user(s) in different contexts of physical activity such as running 110, sitting 112, cycling 114, and playing soccer 116. Different physical activities may produce characteristic sensor signal(s) and affect the physical condition of the user(s) in a characterizing manner. Instant effect (e.g. exhaustion) and future effect (e.g. enhanced condition) may also differ. The mobile device 102 may be coupled to other elements such as other devices 150, 160, and wireless and/or wired network(s) 120 may optionally reside between them as a connecting means.

The mobile device 102 may include a personal activity meter for children and/or other users. The device 102 may be configured to track and store one or more users' daily activities and collect activity points automatically. Preferably the device 102 may automatically identify the current user based on sensor data.

The sensor(s) applied by the mobile device 102 may utilize 2D or 3D accelerometer technology.

The mobile device 102 may contain a display to provide the user thereof with data relative to e.g. physical activity such as identity of the activity and/or other activity information indicative of e.g. related energy consumption. The display may preferably include an OLED (Organic LED) display, which is thinner and consumes less energy than most conventional displays.

The mobile device 102 may include a user input means such as one or more buttons, keys, touch surfaces such as pads or displays, a voice or a speech recognition UI, etc. Further, the device 102 may be accessed by the user via an external device such as a laptop or desktop computer, or a game console, via an available wired or wireless data interface.

The mobile device 102 may include an USB (e.g. 2.0 or more recent) interface for data output and optionally input, e.g. control data input. The mobile device 102 may support different skins and/or themes, which may refer to data visualization on the display and/or on the physical cover of the device 102, and/or to other visible, exterior features of the device 102.

An optional intermediate service entity 150 such as a computer apparatus, e.g. a server or other electronic arrangement such as a selected electronic device, may exploit sensor data for producing activity information, such as preferably user-specific activity points or credits, user profile and/or control data and optionally control signal(s) for a controlled application. The intermediate entity 150 or the target electronic device 160, such as a laptop/desktop/hand-held computer device 162 or a game console 164, may thus exploit the received and/or locally determined activity information such as user identity information, activity type information, and/or activity points or credits for producing control data and/or signal indicative of a user-specific configuration of a target application logic to be controlled (e.g. relative to the availability of the content thereof) by the physical activity performed by the user and the selected characteristics thereof. Content may be added, deleted, or modified in response to the activity or lack thereof, for instance. If no indication of recent physical activity is received by the application, selected features may be temporarily locked until the necessary physical activity has been performed and recorded by the user, for example. A mapping table or other data entity, or a plurality of entities, may be used for linking activity information and control measures.

A mobile device 102 or any electronic device 150, 160 may have a plurality of users. Advantageously the user is identified and verified using an embodiment of a user recognizer algorithm based on the sensor data. The suggested solution is convenient, i.e. practically transparent from the users' standpoint, and potentially also a reliable alternative to manual user identification such as entering a user ID and related password via a keypad or a keyboard in the device.

The activity in question 110, 112, 114, 116 may be recognized using a selected activity recognition technique.

A carrier medium 140 such as an optical disk, a floppy disk, a memory card, a hard disk, a memory chip, or a memory stick may be configured to comprise computer code, e.g. a computer program product, for performing at least part of the tasks for managing a configuration of an application based on sensor data. The program code and/or related data such as sensor data, activity information, and/or control instructions may be provided on a signal carrier. The code and/or the data may be at least partially encrypted using a selected encryption method such as AES (Advanced Encryption Standard).

Parental or other type of control software may be provided that integrates with the target devices' such as consoles'/computers' own (parental) control features. For example, explicit control instructions and/or information for deriving control instructions may be provided to the target devices. For instance, a number of configurable access levels may be constructed for different users. Master user(s) such as parent(s) may be provided with rights to modify the user rights of different end users such as kids. The user rights may include a number of rules linking physical activity and the configuration of the application in view of each end user. For example, playing a game or usage of other type of an application may be blocked or restricted, if the associated user does not bear enough activity points. Certain game(s) or game or other application-related connection(s), e.g. the Internet connection, may be blocked or restricted. Restrictions may be temporal and/or feature-specific, e.g. content-specific. Temporal restriction may determine a maximum time period available to a user to exploit certain content such as a certain feature of the application, or even access the feature. One merely exemplary rule may indicate that the more physically active the user is more playtime or access he/she will have in the light of the gaming or other type of application. Software and/or related data may be encrypted in the mobile device 102 and/or the electronic devices 150, 160 as mentioned above to hinder unauthorized access.

In some embodiments the mobile device or the electronic devices 150, 160 may be self-contained and include all the necessary functionality from obtaining the sensor data to controlling a local application thereof. Tasks may be shared and distributed among available devices 102, 150, and/or 160 embodiment-specifically as understood by a skilled person.

Figure 2:
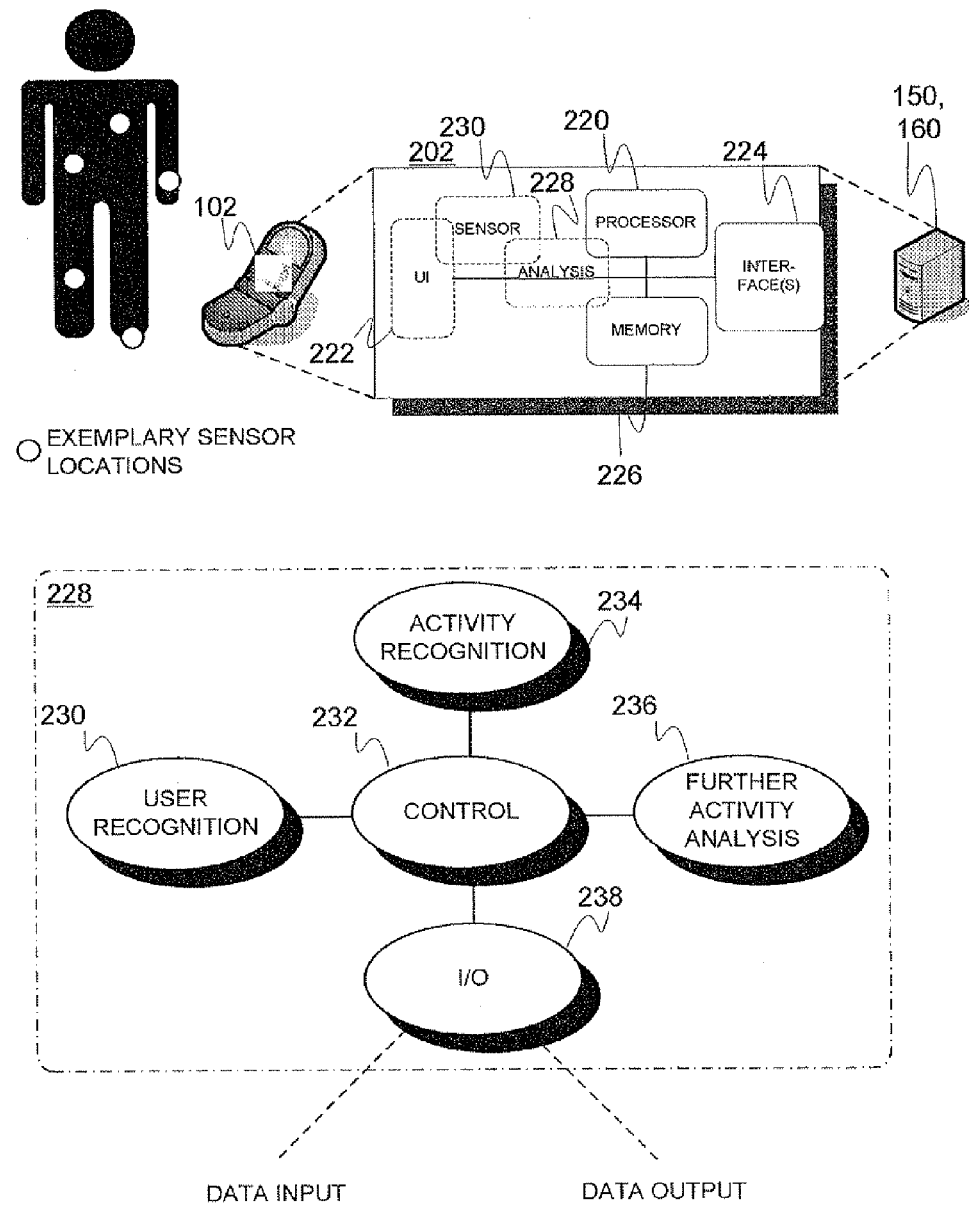
FIG. 2 illustrates embodiments of a mobile device and electronic arrangement (or device) in accordance with the present invention.

FIG. 2 illustrates the internals 202 of an embodiment of an entity such as the mobile device 102, the electronic arrangement 150, and/or the electronic device 160 in accordance with the present invention at least from a functional stand-point. Note that merely exemplary sensor locations are illustrated in the figure as the white circles located in the chest, waist, arm/hand, leg, and foot of a user. The entity in question is typically provided with one or more processing devices capable of processing instructions and other data, such as one or more microprocessors, micro-controllers, DSPs (digital signal processor), programmable logic chips, etc. The processing entity 220 may thus, as a functional entity, physically comprise a plurality of mutually co-operating processors and/or a number of sub-processors connected to a central processing unit, for instance. The processing entity 220 may be configured to execute the code stored in a memory 226, which may refer to e.g. parental control or other software 228 in accordance with the present invention. Software 228 may utilize a dedicated or a shared processor for executing the tasks thereof. Similarly, the memory entity 226 may be divided between one or more physical memory chips or other memory elements. The memory 226 may further refer to and include other storage media such as a preferably detachable memory card, a floppy disc, a CD-ROM, or a fixed storage medium such as a hard drive. The memory 226 may be non-volatile, e.g. ROM (Read Only Memory), and/or volatile, e.g. RAM (Random Access Memory), by nature. The sensor entities 230 may include sensor hardware and/or software elements for obtaining the sensor (raw) data for forwarding and/or analysis such as user recognition, activity recognition and optional further analysis.

The UI (user interface) 222 may comprise a display, e.g. an (O)LED (Organic LED) display, and/or a connector to an external display or a data projector, and a keyboard/keypad or other applicable control input means (e.g. touch screen or voice control input, or separate keys/buttons/knobs/switches) configured to provide the user of the entity with practicable data visualization and/or device control means. The UI 222 may include one or more loudspeakers and associated circuitry such as D/A (digital-to-analogue) converter(s) for sound output, and a microphone with A/D converter for sound input. In addition, the entity may comprise an interface 224 such as at least one transceiver incorporating e.g. a radio part including a wireless transceiver, such as WLAN, Bluetooth or GSM/UMTS transceiver, for general communications with external devices and/or a network infrastructure, and/or other wireless or wired data connectivity means such as one or more wired interfaces (e.g. Firewire or USB (Universal Serial Bus)) for communication with other devices such as terminal devices, control devices, peripheral devices such as external sensors, or network infrastructure(s). It is clear to a skilled person that the entity may comprise few or numerous additional functional and/or structural elements for providing beneficial communication, processing or other features, whereupon this disclosure is not to be construed as limiting the presence of the additional elements in any manner.

Element 228 depicts only one functional example of the analysis logic for the sensor data typically implemented as software stored in the memory 226 and executed by the processing entity 220. In various embodiments the execution of each disclosed action may be shared between multiple entities such as devices or allocated to a certain element of a plurality of co-operating devices for dedicated execution. The logic has an I/O module 238 for interaction with other parts of the host entity including data input (sensor data, control data) and output (activity information etc.). An overall control logic 232 may take care of the coordination of various tasks performed by the logic 228 and optionally derive control data for physical activity-controlled application(s) on the basis of activity information, for example. User recognition block 230 may identify the user associated with the sensor data as described hereinbefore. Likewise, the activity recognition block 234 may identify the particular physical activity as described above. The activity analyzer 236 may derive other activity information such as frequency, intensity, point, credit, and/or profile information. In one embodiment the analyzer 236 may naturally incorporate the user recognition block 230 and/or the activity recognition block 234.

Figure 3:
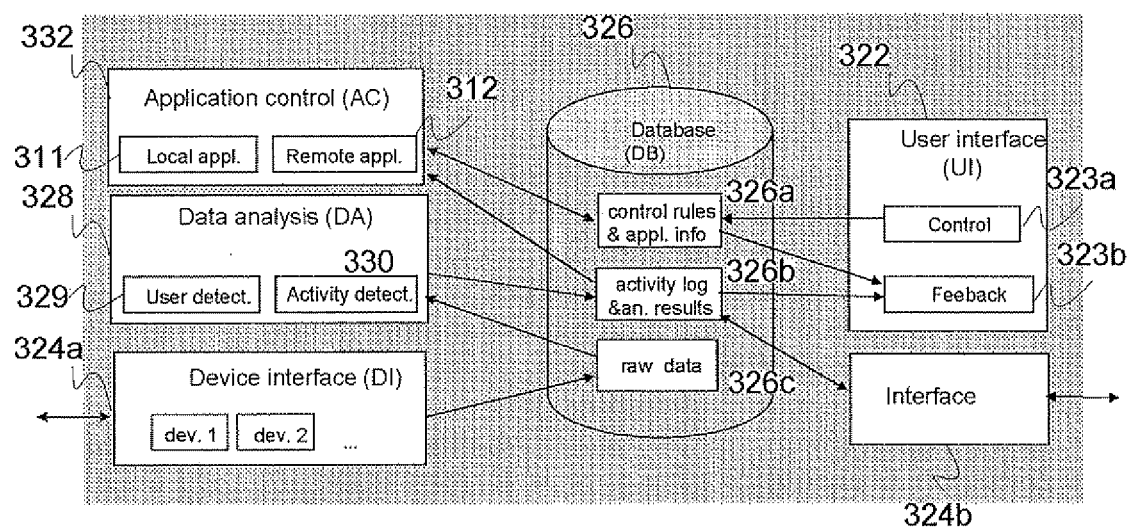
FIG. 3 illustrates an embodiment of software architecture according to the present invention.

FIG. 3 represents an embodiment of general software architecture according to the present invention to be optionally selectively combined with one or more features of any previous embodiment by a skilled person. Also some of the disclosed elements may be left out, modified, or combined use case-specifically. New elements may be correspondingly added. The architecture may be implemented by one or a plurality of devices. For example, the architecture may be at least partially implemented by a mobile device, a laptop/desktop computer device, or a game console.

The architecture may comprise a device interface 324*a* for co-operating with one or more devices, such as mobile devices or sensors, and providing physical activity-related data such as sensor data. Different devices and/or interfaces may be supported.

Data analysis block, or "module", 328 may be configured to analyze the sensor data and provide information about the user's activities including estimates of user identity 329 and activity type 330 in addition to further analysis and resulting information such as activity intensity/energy consumption analysis and associated figures, for example.

Application control block 332 may be configured to control usage of application(s) (local 311 or external 312, e.g. web-based) based on the control logic (rules) and the user's activity information such as activity log entries and/or analysis results.

Database entity 326 comprising one or more databases may be configured to store different data elements such as sensor (raw) data 326c, activity log(s) and/or analysis results 326b, control data, control rules, and/or application information 326a, etc.

UI 322 may be utilized for providing feedback 323b information to user(s), such as to display activity information and related notifications to the user, and/or for enabling control 323a of the entity, such as setting or amending the rules concerning a user's permission to use applications vs. required activity (e.g. per day or other time period).

Interface 324b may be implemented towards external applications and related devices to be controlled and/or an external service such as a web service that may enable verifying, e.g. on the basis of activity log information, that the same activity data has not already been "used" elsewhere, for example. An enlightened user such as an astute kid, for example, could otherwise exploit the points gathered from performing physical exercise multiple times via different access control and/or terminal devices, for instance.

FIG. 4a depicts an example of an accelerometer signal associated with a first physical activity such as (exercise) cycling. The signal may be analyzed by a user recognizer, activity recognizer, and/or a further analyzer.

For instance, wearable accelerometers may be utilized in estimating a user's exercise habits such as schedule, frequency, intensity and/or energy consumption.

Some solutions may be configured to calculate energy consumption on the basis of the power estimate of the sensor signal calculated using a predetermined method. However, e.g. accelerometer(s) attached to a limb of a user may produce acceleration signal the estimated power of which naturally correlates with the movement of the limb, but the correlation with the overall movement and energy consumption of the user may be significantly lower. For example, an accelerometer coupled to the wrist of the cyclist measures only minor movement and "power" during the activity, although the overall activity may considerably increase the energy consumption due to e.g. the legs' intensive movement etc.

Preferably, an activity recognizer utilizing a desired activity recognition technique is used to identify a physical activity based on the sensor signal such as an acceleration signal, which may have relatively low energy e.g. in the case of a cyclist and a wrist accelerometer.

Further, by detecting and calculating the cycles from the signal associated with a cyclic physical activity (such as cycling and many, if not most, other activities like walking, etc.), an estimate of the overall intensity and/or related energy consumption may be obtained with increased accuracy in terms of quantitative analysis. Cycles can be typically detected even from a low-power sensor signal. Detection may apply the analysis of signal amplitude/magnitude values, derivative (e.g. zeros) thereof, and/or time reference, for instance.

The cyclic nature of the sensor signal can be detected also visually in the FIG. 4a. Broken vertical lines are used to visually indicate a single cycle 402 in the signal. The whole signal extract depicted in the figure may represent a period of about 15 seconds in the case of cycling, for example.

FIG. 4b depicts an example of an accelerometer signal associated with, a second physical activity such as rowing. A period 404 is visually indicated in the figure by the two vertical lines. Provided that the periods shown in the FIGS. 4a and 4b are temporally of identical length, a cycle length and/or sensor signal amplitude/magnitude seem to clearly differ between the activities, which may also be applied in activity recognition in addition to intensity/energy consumption analysis. For example, activity type—specific cycle amount—energy consumption association information such as a linkage or mapping table may be applied.

Thus the cycle analysis, particularly when combined with activity type information, may enable quantifying the physical activity, advantageously notwithstanding the particular location of the associated sensor.

It can also be contemplated in the light of FIGS. 4a and 4b that as the signal shapes and/or values may differ between different activities, signal portions associated with different activities may be detected and the overall signal be segmented accordingly.

In order to recognize different activities and their durations from a sensor signal, a long-term sensor signal may indeed be first segmented. The segmentation may refer to determining the beginning and end (instant) of each activity. The segmentation may be executed prior to performing any activity recognition based on the sensor signal.

One principle that may be utilized in segmentation is that most daily activity segments, even if not cyclic as such, are often preceded and/or followed by cyclic activity such as walking. Any one or more of the activity segments of the obtained sensor signal may generally represent cyclic or non-cyclic activity. The detection may be based on setting a threshold for cycle amplitude and duration, and calculating their occurrence relative to time. The detection may be user-configurable such that the user may change the utilized threshold values and/or other detection parameters.

FIG. 4c illustrates an embodiment of a reference signal, or a "reference code", generation method for use in connection with user recognition. FIG. 4d includes visualizations (acceleration-indicating values on y-axis, time/sample count on x-axis) of possible, however merely exemplary signals associated with different method items. The illustrated scenario applies activity-specific, particularly gait/walking-specific, reference signal determination, but also other reference signal(s) could be alternatively or additionally determined. Even a combinatory reference signal relating to a plurality of activities could be established.

At start-up 410 the applied gear, such as a pod or other device comprising preferably at least one sensor such as a 3D accelerometer or three one-dimensional accelerometers functionally considered as a 3D accelerometer hereinafter, is obtained, configured and activated.

At 412, the device comprising the 3D accelerometer and being located in the subject's pocket, for instance, records motion activities of a longer duration (potentially hours). The obtained acceleration data, optionally in a form of a data file, may be provided after capturing phase to an external computer device for analysis. At 412b, three different acceleration signals, one per axis, are depicted. The gathered data may relate to several hours of 3D acceleration signal.

At 414, a number of (motion) activity segments are extracted from the data. Each segment, or "pattern", may relate to a certain activity such as walking, running, jumping, etc. At 414b, three signals from three activities, namely walking, running, and jumping (from left to right) are visualized (one acceleration signal out of the three available provided by a 3D accelerometer is shown in each graph).

Further, the longest walk segment may be chosen for gait code construction. The longest walk segment may thus be extracted from the overall segmented data. Three acceleration signals of the 3D accelerometer potentially relating to such a segment are shown at 414c for illustrative purposes only.

At 416, these three signals of the longest walk segment corresponding to the three axes of acceleration are summed into one signal, a so-called basic sum signal.

At 416b, an example of the sum signal is illustrated. The 3D accelerometer may practically be in any spatial orientation and in many different locations, but the sum signal still advantageously exhibits unique properties for each individual.

At 418, a number of other signals may be generated. These signals can be, e.g., 1) derivative of the basic sum signal, "derivative signal" and/or 2) the "normalized signal" for which the three original acceleration signals provided by a 3D accelerometer may be normalized (relative to zero level) and summed together.

At 420, a plurality of sub-elements such as the step pairs (left and right step together) are separated from each other utilizing at least one available source signal such as the aforementioned basic sum, derivative or normalized signal. At 420b, exemplary step pairs are depicted. A set of n step pairs may be established for further analysis. The step pair set may include, e.g., the step pairs extracted from the 1) basic sum signal, 2) "derivative signal" and/or 3) "normalized signal".

At 422, the sub-elements such as the step pairs may be normalized and/or otherwise processed. For instance, the amplitude and the sample amount of step pairs may be normalized into amplitude range of ±1.0 and sample amount of 256. As a result, the different step pairs will be of equal length and of equal amplitude range. In fast walking the step pairs can be, e.g., 70 samples long but they may be made (extended, for example), e.g., 256 samples long (sampling frequency may be about 80 Hz). Normalization enables comparing different step pairs since quite typically walking frequency and acceleration values vary.

At 424, a number of sub-elements, i.e. the step pairs in the depicted case, may be selected for reference construction according to desired criteria. For example, the best normalized step pairs may be chosen for (gait) reference code construction, wherein "the best normalized step pair" may refer to a normalized step pair which has the best average correlation with other normalized step pairs. A desired percentage such as about 20%, 40% or 60% of the normalized step pairs may be chosen, for instance.

At 426, the reference gait code is constructed through utilization of the chosen preferably normalized step pairs by summing them up, for example. The reference gait code may be stored as associated with the related user identity for future recognition purposes.

At 426b, the shown three graphs may refer to e.g., basic, derivative and normalized signals, wherein each graph may be considered to show normalized step pair data of one of the aforesaid signal types. Accordingly, the gait code may be a multi-part code. The first part of the gait code (e.g. values 1-256 at 426b) may be made of, e.g., the basic signal, the second part (values 257-512) of, e.g., the "derivative signal" and the third part (values 513-768) of, e.g., the "normalized signal". Additionally or alternatively, the gait code could be constructed from other kinds of signals.

Conceptually, the gait code may be considered as the "digital fingerprint" of the particular user. The gait codes may be determined for a plurality of users. For every user, it is advantageously of the same normalized length. It can be, e.g., constructed of a predetermined number, such as the aforementioned 256, of basic signal values, "derivative signal" values and "normalized signal" values, thus making the resulting aggregate gait code e.g. 768 samples long. As alluded above, the gait codes may be of any length as long as they are advantageously normalized, of the same length for all users and include the same (corresponding) signals.

Phases 428 and 430 relate to user recognition based on available user-specific reference code(s) and sensor data relating to a user to be identified.

At 428, a gait code is first established to the unknown or at least unverified user (the user may indeed in some use scenarios first indicate his/her identity, but it may be still be verified by the disclosed method) according to the above guide-lines on the basis of the acquired sensor data.

In verification, the gait code of the unknown user may be correlated with the known gait code of the claimed identity. If the correlation is high enough (item 430) according to the utilized criterion, the two gait codes are a match and the claimed identity of the unknown person is verified.

In identification the gait code of the unknown user is correlated with gait codes stored in the user database. The best match, i.e. highest correlation, may be considered (item 430) as the identification result. Additionally, a minimum correlation threshold may be optionally applied such that if even the best match provides so low correlation that it remains below the threshold, identification may be considered as unsuccessful and the user remains anonymous from the standpoint of the user recognizer.

The method execution is ended at 432. Reference codes may be determined for users and the relating method items performed flexibly upon need. Also the recognition phases 428, 430 may be executed to identify the user associated with the provided activity data.

FIG. 5 discloses, by way of example only, a method flow diagram in accordance with an embodiment of the present invention. At 502 an entity such as a mobile device, electronic arrangement, electronic device, system, or a desired combination of those in accordance with the present invention is obtained and configured, for example, via installation and execution of related software and hardware, such as sensor, entities for executing the method. At 504 sensor data is obtained which may refer to receiving the data from the sensor or a device comprising it or being connected thereto. At 506, an indication of the user associated with the physical activity sensor data is obtained, which may refer to receiving such indication from an external entity or determining it on the basis of the sensor data, for instance. At 508, an indication of the activity is obtained, which may refer to receiving such indication from an external entity or determining it on the basis of the sensor data, for instance. At 510, further analyses such as frequency analysis, intensity analysis, and/or energy consumption analysis relative to the physical activity may be conducted, or at least the relevant analysis results may be received from an external entity. Activity information such as activity points or credits to be used with an application may be defined, for example. At 512, the identified user's configuration of application logic, such as access and/or one or more other features, e.g. content features, relative to the application logic, based on the identified activity and optionally other activity information derived utilizing the sensor data, is modified. If the entity executing the method is not hosting the target (end) application logic to be controlled by itself, it may at least provide information enabling to modify it, such as points/credits or more explicit control data, via an applicable interface. Method execution is ended at 514. The broken arrow on the right depicts the potentially substantially continuous nature of method execution. The mutual ordering and overall presence of the method steps, as already deliberated above, may be altered by a skilled person based on the requirements set by each particular use scenario.

Consequently, a skilled person may on the basis of this disclosure and general knowledge apply the provided teachings in order to implement the scope of the present invention as defined by the appended claims in each particular use case with necessary modifications, deletions, and additions. In some use scenarios identification of the user may not be necessary, for example. By the principles set forth hereinbefore, a target (application) device hosting the end application, such as a game, to be user-specifically controlled responsive to the physical activity by the user, may be configured to obtain indication of the user, activity type, and/or other activity information such as activity points, activity profile and/or other evaluation of the activity, and further configured to control the preferably user-specific configuration of the application and optionally the device in general, such as a plurality of applications and/or optional hardware features controlled by them, accordingly. Control of the configuration may include rewarding a physically active user with lengthened access time and/or provision of additional content, facilitating access to content, and/or facilitating access to supplementary services such as a web service relative to the application, for example. Additionally or alternatively, punitive control such as reducing the access time or limiting the accessible content is fully possible in response to the detected low physical activity or complete lack thereof during e.g. a predetermined time window or due to other reason derived utilizing the sensor data.

Recommendations for performing or refraining from physical activity may be produced preferably user-specifically. A recommendation may be based on sensor data analysis. Too much (exhaustive) monitored physical activity during a predetermined period may convert into a recommendation to refrain from physical activity, for example, and vice versa. The mobile device, electronic arrangement, the system, and/or the (end) application device such as a game console may provide a recommendation to the user visually, e.g. via a display, and/or by audio output e.g. via a loudspeaker, and/or through the use of tactile or some other means.

The invention claimed is:

1. A mobile device for a plurality of users, said users being identifiable based on sensor data, comprising
   a sensor data storage for obtaining sensor data indicative of physical activity associated with a user monitored via a sensor,
   a user recognizer for identifying the user from said plurality of identifiable users on the basis of the sensor data obtained,
   an activity recognizer for identifying the physical activity of the identified user, such as a sports activity, on the basis of the sensor data obtained,
   an analyzer for measuring an intensity or energy consumption associated with the physical activity performed, and
   an interface for providing an indication of a user identity, indication of the physical activity, and an indication of said intensity or energy consumption, to an application logic to enable modifying the identified user's configuration relative to said application logic incorporating rewarding the user for performing the physical activity, said application logic being either local or external relative to the mobile device, wherein said rewarding comprises allocating the level of user rights of the associated user relative to a number of applications responsive to the physical activity.

2. The mobile device of claim 1, comprising at least one sensor selected from the group consisting of: an accelerometer, a gyroscope, a pedometer, a pulse meter, a movement sensor, a pressure sensor, a location sensor or other location determination entity, a distance sensor, a velocity sensor, a speed sensor, and a blood oxygen sensor.

3. The mobile device of claim 1, comprising a GPS (Global Positioning System) receiver for position sensing.

4. The mobile device of claim 1, wherein the user recognizer is configured to utilize a user-specific, and optionally an activity-specific, reference signal and/or other reference data to identify the user on the basis of the sensor data.

5. The mobile device of claim 1, wherein the user recognizer is configured to utilize a user-specific, and optionally an activity-specific, reference signal and/or other reference data to identify the user on the basis of the sensor data, and wherein a plurality of references is associated with a certain user, preferably at least one reference per activity to be identified.

6. The mobile device of claim 1, wherein the user recognizer is configured to utilize a user-specific, and optionally an activity-specific, reference signal and/or other reference data to identify the user on the basis of the sensor data, and wherein a plurality of references is associated with a certain user, preferably at least one reference per activity to be identified, and further wherein a sum signal based on a plurality of acceleration signals corresponding to an activity-specific segment of sensor data is formed and utilized as such and/or in modified form to extract a plurality of sub-elements therefrom, such as step pairs in connection with walking activity, to be applied for determining the activity-specific reference.

7. The mobile device of claim 1, wherein the user recognizer is configured to utilize a user-specific, and optionally an activity-specific, reference signal and/or other reference data to identify the user on the basis of the sensor data, and wherein a plurality of references is associated with a certain user, preferably at least one reference per activity to be identified, and further wherein a sum signal based on a plurality of acceleration signals corresponding to an activity-specific segment of sensor data is formed and utilized as such and/or in modified form to extract a plurality of sub-elements therefrom, such as step pairs in connection with walking activity, to be applied for determining the activity-specific reference, and wherein a number of said sub-elements are processed, such as normalized and summed together, to establish the activity-specific reference.

8. The mobile device of claim 1, wherein the user recognizer is configured to utilize at least one analysis tool for identifying the user based on the sensor data, the tool being selected from the group consisting of: cross correlation, a number of Fourier coefficients, neural network, and structured pattern recognition.

9. The mobile device of claim 1, wherein the activity recognizer is configured to utilize an activity-specific, and optionally user-specific, reference signal and/or other reference data to identify the activity on the basis of the sensor data.

10. The mobile device of claim 1, comprising a remote identification device such as an RFID (Radio Frequency Identification) or NFC (Near Field Communication) tag, preferably provided with a unique ID.

11. The mobile device of claim 1, comprising application logic, optionally a game application or other end application or a control application 12.

12. An electronic arrangement, optionally an electronic device or a plurality of at least functionally connected devices, for controlling and optionally hosting one or more applications for a plurality of users identifiable based on sensor data, said arrangement comprising an input collector for obtaining sensor data, such as accelerometer data, acquired by a mobile device, and indicative of physical activity associated with a user, such as sports activity,
a user recognizer for identifying the user of the mobile device from said plurality of users on the basis of the sensor data,
an activity recognizer for identifying the physical activity of the identified user on the basis of the sensor data,
an analyzer for determining an intensity or energy consumption associated with the physical activity, and
a control entity configured to modify or at least provide information enabling to modify the user's configuration of an application logic incorporating rewarding the user for performing the physical activity, based on the physical activity and an indication of said intensity or energy consumption, said application logic being either local or external relative to the electronic arrangement, wherein said rewarding comprises allocating the level of user rights of the associated user relative to a number of applications responsive to the physical activity.

13. The arrangement of claim 12, wherein the user recognizer is configured to analyze the sensor data for identifying the user based on the sensor data using at least one analysis method or element selected from the group consisting of: cross correlation, a number of Fourier coefficients, neural network, and structured pattern recognition.

14. The arrangement of claim 12, configured to determine the number of cycles of a cyclic physical activity during a predetermined time period represented by the sensor data.

15. The arrangement of claim 12, configured to determine the number of cycles of a cyclic physical activity during a predetermined time period represented by the sensor data, and further configured to utilize the determined number of cycles and an indication of the identified activity to establish an estimate of an overall energy consumption of the user relative to the period.

16. The arrangement of claim 12, configured to segment the sensor data based on the detection of cyclic physical activity and related cycles in the data.

17. The arrangement of claim 12, configured to provide activity information comprising at least one information element selected from the group consisting of: the user's or user group's activity profile, activity rank, activity class, activity points, activity credits, energy consumption information, frequency information, duration information, numerical information, symbolic information, textual information, qualitative information, quantitative information, stressfulness information, training effect information, and intensity information.

18. The arrangement of claim 12, configured to modify the configuration via the control of at least one configuration element selected from the group consisting of: a parental control feature, a game feature, an application content feature, a personal training feature, a training log, a locked feature, a reward feature, a punishment feature, a bonus feature, activation feature, deactivation feature, an instructive feature, and a communications feature.

19. A system comprising a mobile device for use by a plurality of users identifiable based on sensor data and at least one electronic device external thereto, said system comprising a sensor for obtaining data indicative of physical activity associated with a user,
a user recognizer for identifying the user from said plurality of users on the basis of the sensor data obtained,
an activity recognizer for identifying the physical activity of the identified user on the basis of the sensor data obtained,
an analyzer for determining an intensity or energy consumption associated with the physical activity performed, and
a control entity configured to modify or at least provide information enabling to modify the user's configuration of an application logic incorporating rewarding the user for performing the physical activity, based on the physical activity and said intensity or energy consumption, wherein said rewarding comprises allocating the level of user rights of the associated user relative to a number of applications responsive to the physical activity.

20. A method for controlling the configuration, optionally access and/or one or more other features, of a number of applications in an electronic device from the standpoint of a particular user, comprising obtaining an indication of the identity of the user determined based on sensor data associated with physical activity by the user and provided by a sensor device for use by a plurality of users identifiable based on sensor data,
obtaining an indication of the user's physical activity identified based on the sensor data,
obtaining an indication of an intensity or energy consumption of the physical activity by the user, and
modifying or at least providing information enabling to modify the user's configuration of an application logic incorporating rewarding the user for performing the physical activity based on the physical activity and said indication of intensity or energy consumption, wherein said rewarding comprises allocating the level of user rights of the associated user relative to said number of applications responsive to the physical activity.

21. A computer program product in a non-transient computer readable storage medium for controlling the configuration of a number of applications in an electronic device from the standpoint of a particular user, comprising program code for obtaining an indication of the identity of the user determined based on sensor data associated with physical activity by the user and provided by a sensor device for use by a plurality of users identifiable based on sensor data, for obtaining an indication of the user's physical activity identified based on the sensor data, for obtaining an indication of the intensity or energy consumption associated with the physical activity, and for modifying or at least providing information enabling to modify the identified user's configuration of an application logic incorporating rewarding the user for performing the physical activity based on the identified activity and said indication of said intensity or energy consumption, wherein said rewarding comprises allocating the level of user rights of the associated user relative to said number of applications responsive to the physical activity.

* * * * *